US010821164B2

(12) United States Patent
Hoft et al.

(10) Patent No.: US 10,821,164 B2
(45) Date of Patent: Nov. 3, 2020

(54) PEPTIDES FOR INDUCING CHAGAS DISEASE RESPONSES

(71) Applicants: SAINT LOUIS UNIVERSITY, St. Louis, MO (US); EPIVAX, INC., Providence, RI (US)

(72) Inventors: Daniel Hoft, St. Louis, MO (US); Chris Eickhoff, St. Louis, MO (US); Annie De Groot, Providence, RI (US)

(73) Assignees: Saint Louis University, St. Louis, MO (US); EPIVAX, INC., Providence, RI (US)

( * ) Notice: Subject to any disclaimer, the term of this patent is extended or adjusted under 35 U.S.C. 154(b) by 0 days.

(21) Appl. No.: 15/738,209

(22) PCT Filed: Jun. 6, 2016

(86) PCT No.: PCT/US2016/035982
§ 371 (c)(1),
(2) Date: Dec. 20, 2017

(87) PCT Pub. No.: WO2016/209598
PCT Pub. Date: Dec. 29, 2016

(65) Prior Publication Data
US 2018/0185462 A1    Jul. 5, 2018

Related U.S. Application Data

(60) Provisional application No. 62/183,513, filed on Jun. 23, 2015.

(51) Int. Cl.
*A61K 39/00* (2006.01)
*A61K 38/00* (2006.01)
*A61K 39/005* (2006.01)
*C12N 9/00* (2006.01)
*C12N 9/24* (2006.01)
*A61K 35/15* (2015.01)

(52) U.S. Cl.
CPC .......... *A61K 39/005* (2013.01); *A61K 39/00* (2013.01); *C12N 9/00* (2013.01); *C12N 9/2402* (2013.01); *C12Y 302/01018* (2013.01); *A61K 35/15* (2013.01); *A61K 38/00* (2013.01); *A61K 2039/5154* (2013.01); *A61K 2039/54* (2013.01); *A61K 2039/545* (2013.01); *Y02A 50/414* (2018.01)

(58) Field of Classification Search
None
See application file for complete search history.

(56) References Cited

U.S. PATENT DOCUMENTS

| 7,060,676 | B2 * | 6/2006 | Chuenkova | A61K 35/68 514/17.7 |
| 7,892,555 | B2 * | 2/2011 | Tarleton | A61K 39/005 424/184.1 |
| 8,114,412 | B2 * | 2/2012 | Chuenkova | A61K 35/68 424/191.1 |
| 8,900,598 | B2 * | 12/2014 | de Baeremaecker Barros | A61K 39/005 424/269.1 |
| 9,028,844 | B2 * | 5/2015 | Contreras | A61K 38/16 424/269.1 |
| 9,290,757 | B2 * | 3/2016 | Madison | G01N 33/6842 |
| 9,662,378 | B2 * | 5/2017 | de Baeremaecker Barros | A61K 39/005 |
| 10,081,801 | B2 * | 9/2018 | Mikkelsen | A61K 31/702 |
| 10,213,500 | B2 * | 2/2019 | de Baeremaecker Barros | A61P 37/04 |
| 10,533,164 | B2 * | 1/2020 | Mikkelsen | C12N 9/2402 |
| 2002/0137667 | A1 * | 9/2002 | Chuenkova | A61K 35/68 514/8.4 |
| 2005/0142116 | A1 * | 6/2005 | Higuchi | A61K 31/18 424/93.4 |
| 2005/0158347 | A1 * | 7/2005 | Tarleton | A61K 39/005 424/269.1 |
| 2006/0229247 | A1 * | 10/2006 | Chuenkova | A61K 35/68 514/8.4 |
| 2009/0117593 | A1 * | 5/2009 | Chuenkova | C07K 14/44 435/7.21 |
| 2010/0297173 | A1 * | 11/2010 | Tarleton | A61K 39/005 424/208.1 |
| 2011/0038887 | A1 * | 2/2011 | Contreras | A61K 38/16 424/191.1 |
| 2011/0076297 | A1 |  | 3/2011 | Hoft et al. |
| 2012/0201780 | A1 * | 8/2012 | Chuenkova | A61K 35/68 424/85.2 |
| 2012/0276131 | A1 * | 11/2012 | Coustou Linares | C12N 9/1081 424/191.1 |
| 2014/0178891 | A1 * | 6/2014 | Higuchi | A61K 38/47 435/6.15 |
| 2015/0056243 | A1 * | 2/2015 | de Baeremaecker Barros | A61K 39/005 424/191.1 |

(Continued)

FOREIGN PATENT DOCUMENTS

WO    WO-2007107488 A2 *  9/2007 ............. A61K 38/16
WO    WO-2011058080 A1 *  5/2011 ........... C12N 9/1081

(Continued)

OTHER PUBLICATIONS

Cuevas et al, Infection and Immunity, Oct. 2003, 71/10:5739-5749 (Year: 2003).*
Giddings et al, Infection and Immunity, Mar. 2010. 78/3:1333-1338 (Year: 2010).*
Cai et al, Journal of Immunology, May 2015, vol. 194, No. 1, Suppl. Suppl 1, Abstract No. 144.10 abstract only (Year: 2015).*
Giddings et al, Infection and Immunity, Oct. 2006, 74/10:5549-5560 (Year: 2006).*

(Continued)

*Primary Examiner* — Nita M. Minnifield
(74) *Attorney, Agent, or Firm* — Parker Highlander PLLC

(57) ABSTRACT

The present disclosure relates to vaccine formulations and their use in treating and preventing Chagas Disease.

16 Claims, 2 Drawing Sheets
Specification includes a Sequence Listing.

(56) References Cited

U.S. PATENT DOCUMENTS

| | | | |
|---|---|---|---|
| 2016/0076013 A1* | 3/2016 | Mikkelsen | C12N 9/2402 514/53 |
| 2017/0290896 A1* | 10/2017 | de Baeremaecker Barros | A61K 39/005 |
| 2018/0185462 A1* | 7/2018 | Hoft | A61K 39/005 |
| 2019/0119661 A1* | 4/2019 | Mikkelsen | A61K 31/702 |

FOREIGN PATENT DOCUMENTS

| | | | |
|---|---|---|---|
| WO | WO 2014/153153 | 9/2014 | |
| WO | WO-2016209598 A1 * | 12/2016 | A61K 39/005 |

OTHER PUBLICATIONS

Hoft et al, Faseb J, 17, No. 7, C24, 2003. (conference abstract: The American Association of Immunologists 90th Anniversary Annual Meeting, Denver, Colorado, USA, May 6-10, 2003) (abstract only) (Year: 2003).*

Blase, "Effects of differential T cell priming on Trypanosoma cruzi immunity: Studies of CD4+ T cells induced by natural infection, vaccination and Th17 differentiation" Dissertation Abstracts International, (2014) vol. 76, No. 1B(E). Order No. AAI3642880. ProQuest Dissertations & Theses. (Year: 2014).*

Grandgenett et al, Molecular and Biochemical Parasitology, 2000, 110:409-415 (Year: 2000).*

Burgos et al, PLoS One, 2013, 8(3): e58967. doi:10.1371/journal. pone.0058967. published: Mar. 11, 2013 (Year: 2013).*

Sullivan et al, J. Immunology. Jan. 2015, 194:1806-1818. prepublished online Jan. 16, 2015 (Year: 2015).*

Eickhoff et al, Human Vaccines and Immunotherapeutics, Sep. 2015, 11/9:2322-2328 (Year: 2015).*

El-Sayed et al, Science, Jul. 15, 2005, 309(5733):404-409 (Year: 2005).*

Alvarez et al., "HLA Class I-T Cell Epitopes from trans-Sialidase Proteins Reveal Functionally Distinct Subsets of CD8+ T Cells in Chronic Chagas Disease," PLoS One, 2(9):e288, 2008.

Araujo et al., "Genetic vaccination against experimental infection with myotropic parasite strains of Trypanosoma cruzi," Mediators Inflamm., 2014:605023, 2014.

Atwood et al., "The Trypanosoma cruzi proteome," Science, 309:473-476, 2005.

Balouz et al., "Mapping antigenic motifs in the Trypomastigote Small Surface Antigen (TSSA) from Trypanosoma cruzi," Clin. Vaccine Immunol, 22(3):304-312, 2015.

Bottino et al., "Chagas disease-specific antigens: characterization of epitopes in CRA/FRA by synthetic peptide mapping and evaluation by ELISA-peptide assay," BMC Infect Dis, 13:568, 2013.

De Groot et al., "Immunoinformatic comparison of T-cell epitopes contained in novel swine-origin influenza A (H1N1) virus with epitopes in 2008-2009 conventional influenza vaccine," Vaccine, 27:5740-5747, 2009.

De Groot et al., "Reducing risk, improving outcomes: Bioengineering less immunogenic protein therapeutics," Clin Immunol., 131:189-201, 2009.

Eickhoff et al., "An immunoinformatic approach for identification of Trypanosoma cruzi HLA-A2-restricted CD8+ T cell epitopes," Human Vacc. Immunother., 11(9):2322-2328, 2015.

Eickhoff et al., "Co-administration of a plasmid DNA encoding IL-15 improves long-term protection of a genetic against Trypanosoma cruzi," PLoS NTD, 5:e983, 2011.

El Sayed et al., "The genome sequence of Trypanosoma cruzi, etiologic agent of Chagas disease," Science, 309:409-415, 2005.

Fujimura et al., "DNA Sequences Encoding CD4+ and CD8+ T-Cell Epitopes Are Important for Efficient Protective Immunity Induced by DNA Vaccination with a Trypanosoma cruzi Gene," Infect Immun., 69:5477-5486, 2001.

Hoft et al., "Trans-Sialidase Recombinant Protein Mixed with CpG Motif-Containing Oligodeoxynucleotide Induces Protective Mucosal and Systemic Trypanosoma cruzi Immunity Involving CD8+ CTL and B Cell-Mediated Cross-Priming," J. Immunol., 179:6889-900, 2007.

International Preliminary Report on Patentability issued in corresponding PCT Application No. PCT/US2016/035982, dated Jan. 4, 2018.

International Search Report and Written Opinion issued in corresponding PCT Application No. PCT/US2016/035982, dated Dec. 2, 2016.

Lasso et al., "Frequency of specific CD8+ T cells for a promiscuous epitope derived from Trypanosoma cruzi KMP—11 protein in chagasic patients," Parasite Immunol., 32:494-502, 2010.

Laucella et al., "Changes in Trypanosoma cruzi-Specific Immune Responses after Treatment: Surrogate Markers of Treatment Efficacy," Clin. Infect. Dis., 49:1675-1684, 2009.

Laucella et al., "Frequency of Interferon-γ-Producing T Cells Specific for Trypanosoma cruzi Inversely Correlates with Disease Severity in Chronic Human Chagas Disease," J. Infect. Dis., 189:909-18, 2004.

Martin et al., "CD8+ T-Cell responses to Trypanosoma cruzi are highly focused on strain-variant trans-sialidase epitopes," PLoS Pathog, 2:e77, 2006.

Mendes et al., "Identification of Strain-Specific B-cell Epitopes in Trypanosoma cruzi Using Genome-Scale Epitope Prediction and High-Throughput Immunoscreening with Peptide Arrays," PLoS Negl Trop Dis, 7:e2524, 2013.

Moise et al., "In silico-accelerated identification of conserved and immunogenic variola/vaccinia T-cell epitopes," Vaccine, 27:6471-6479, 2009.

Reche and Reinherz, "PEPVAC: a web server for multi-epitope vaccine development based on the prediction of supertypic MHC ligandan," Nucleic Acids Res., 33:W138-42, 2005.

Rosenberg et al., "CD8+ T cells specific for immunodominant trans-sialidase epitopes contribute to control of Trypanosoma cruzi infection but are not required for resistance," J. Immunol, 185:560-8, 2010.

Sullivan et al., "Deficiency of Antigen-Specific B Cells Results in Decreased Trypanosoma cruzi Systemic but Not Mucosal Immunity Due to CD8 T Cell Exhaustion," J. Immunol., 194:1806-1818, 2015.

Tarleton, "Depletion of CD8+ T cells increases susceptibility and reverses vaccine-induced immunity in mice infected with Trypanosoma cruzi," J. Immunol., 144:717-724, 1990.

Wizel et al., "Human Infection with Trypanosoma cruzi Induces Parasite Antigen-Specific Cytotoxic T Lymphocyte Responses," J. Clin. Invest., 102(5):1062-1071, 1998.

Wizel et al., "Identification of Trypanosoma cruzi trans-sialidase family members as targets of protective CD8+ TC1 responses," J. Immunol., 159:6120-30, 1997.

* cited by examiner

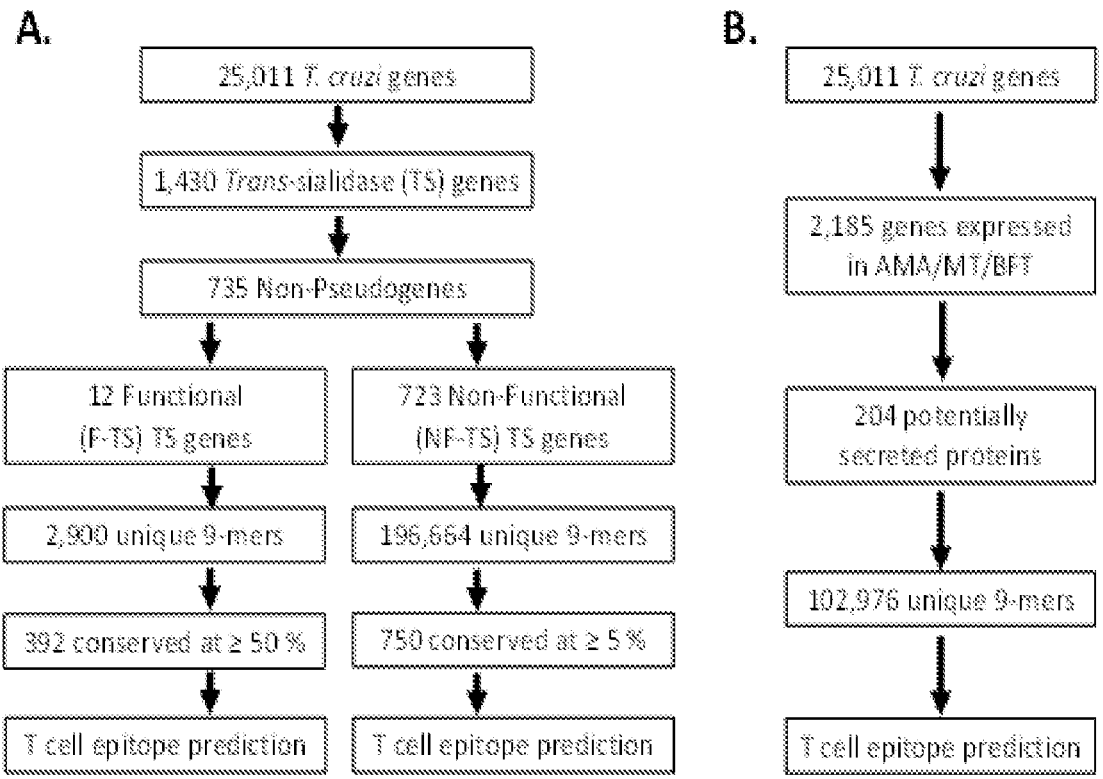
FIGS. 1A-B

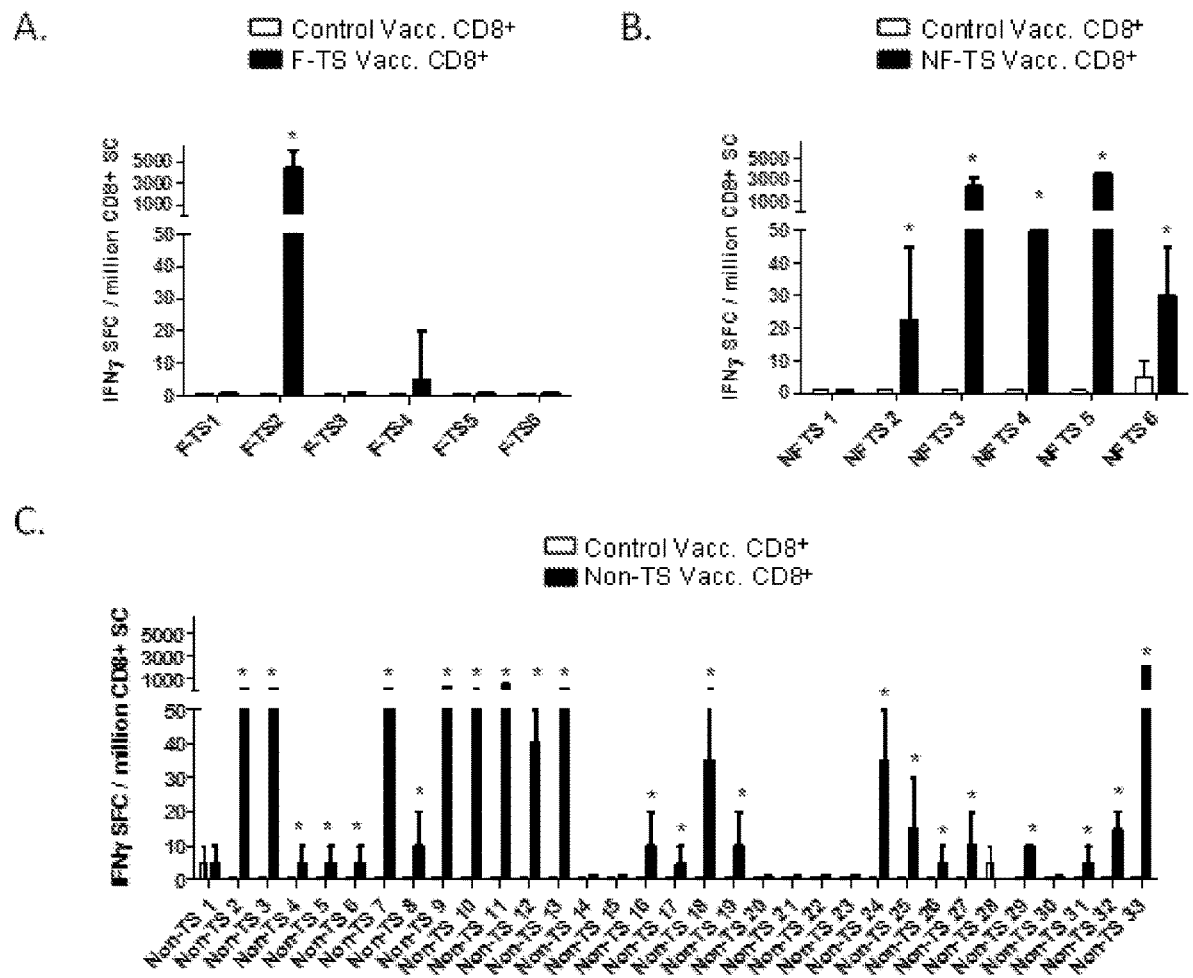
FIGS. 2A-C

SEQUENCE LISTING

```
<160> NUMBER OF SEQ ID NOS: 30

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

Glu Val Tyr Ser Leu Val Phe Ala Arg Leu
1               5                   10

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Asn Val Leu Leu Tyr Asn Arg Pro Leu
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Trp Leu Thr Asp Asn Thr His Ile Val
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Asn Thr Trp Arg Asp Glu Tyr Leu Gly Val
1               5                   10

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Lys Val Gly Ser Asp Val Phe Ala Val
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Arg Val Phe Thr Ser Ala Val Leu Leu
1               5
```

```
<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Val Val Met Ala Cys Leu Val Pro Ala
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Thr Leu Leu Phe Gln Val Leu Leu Leu
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptide

<400> SEQUENCE: 9

Arg Ile Gly Asp Val Cys Ala Glu Val
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Leu Leu Phe Gln Val Leu Leu Leu Cys
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Tyr Val Val Ser Leu Leu Ala Asp Thr
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide

<400> SEQUENCE: 12

Ala Leu His Ser Leu Val Leu Phe Leu
1               5
```

<210> SEQ ID NO 13
<211> LENGTH: 9
<212> TYPE: PRT
<213> ORGANISM: Artificial sequence
<220> FEATURE:
<223> OTHER INFORMATION: Synthetic peptide

<400> SEQUENCE: 13

Ala Val Ile Pro Ser Thr Phe Pro Leu
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Ser Leu Phe Pro Phe Phe Phe Phe Val
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic peptide

<400> SEQUENCE: 15

Phe Leu Val Asp Thr Ile Tyr Ser Ile
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Tyr Leu Asp Ala Val Phe Tyr Pro Leu
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic peptide

<400> SEQUENCE: 17

Ser Leu Leu Cys Val Ile Ser Phe Ile
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Ala Leu Leu Pro Trp Leu Leu Val Leu
1               5

```
<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Leu Met Asn Asp Val Trp Phe Ser Leu
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Phe Leu Ile Phe Arg Phe Met Val Leu
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic peptide

<400> SEQUENCE: 21

Phe Met Ala Cys His Thr Asn Pro Ile
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Met Met His Pro Phe Leu Cys Ala Leu
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Ser Met Asn Ala Gly Leu Tyr Leu Leu
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

Ala Val Phe Asp Ser Val Tyr Ser Val
1               5

<210> SEQ ID NO 25
```

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 25

Phe Leu Asn Gln Phe Gly Thr Arg Leu
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Ser Met Gln Glu Tyr Arg His Met Val
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Ser Val Val Ser Val Phe Phe Leu Leu
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Gln Met Leu His Asn Val Ala Ser Leu
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Met Met Met Thr Gly Arg Val Leu Leu
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic peptide

<400> SEQUENCE: 30

Thr Leu Met Asp Phe Cys Pro Tyr Ile
1               5
```

US 10,821,164 B2

PEPTIDES FOR INDUCING CHAGAS DISEASE RESPONSES

The present application is a national phase application under 35 U.S.C. § 371 of International Application Serial No. PCT/US2016/035982, filed Jun. 6, 2016, which claims benefit of priority to U.S. Provisional Application Ser. No. 62/185,513, filed Jun. 23, 2015, the entire contents of each of which are hereby incorporated by reference.

The invention was made with government support under grant no. NIH R21-AI099514 awarded by the National Institutes of Health. The government owns certain rights in the invention.

Pursuant to 37 C.F.R. § 1.821(c), a sequence listing is submitted herewith as an ASCII compliant text file named "USTLP0056US_ST25.txt", created on Dec. 19, 2017 and having a size of 6 kilobytes. The content of the aforementioned file is hereby incorporated by reference in its entirety.

BACKGROUND

1. Field

The present disclosure relates generally to the fields of parasitology and immunotherapy. More particularly, it concerns the identification of immunostimulatory peptides and the development of peptide vaccines for the treatment and prevention of Chaga's Disease.

2. Description of Related Art

Over 1 billion people are infected with neglected tropical diseases (NTD), which predominantly affect poor people in developing countries (World Health Organization, 2009). Chagas disease is one such NTD, caused by chronic infection with the protozoan parasite *Trypanosoma cruzi*. An estimated 11 million people are infected with this tropical parasite resulting in thousands of deaths per year (Rassi et al., 2010). Due to emigration mostly, Chagas disease is now a public health concern in many regions and countries throughout the world. For example, 300,000 people in the United States are estimated to be infected with *T. cruzi*. (Bern & Montgomery, 2009). Up to 40% of infected individuals go on to develop clinical manifestations associated with chronic Chagas disease which include both cardiac (cardiomyopathy) and gastrointestinal abnormalities (megaesophogus and megacolon) (Rassi et al., 2010). There are currently no vaccines available for prevention of *T. cruzi* infection. Drugs including nifurtimox and benznidazole have proven effective at treating *T. cruzi* infection, but both are associated with many adverse reactions and are not well tolerated in a large number of patients (Jackson et al., 2010). However, the utilization of these drugs has challenged and disproven the belief that the underlying cause of chronic Chagas disease is autoimmunity (Brandariz et al., 1995; Schijman et al., 2004; Apt et al., 1998; Viotti et al., 2006 and Marcon et al., 2011). In recent years there have been significant efforts to develop prophylactic and therapeutic vaccines as well as new drugs for the prevention and treatment of Chagas disease.

*T. cruzi* is primarily transmitted to humans by insect-derived metacyclic trypomastigotes (MT) present in the excreta of triatomine (reduviid) insects (Rassi et al., 2010). Epimastigotes present in the insect midgut differentiate into highly infectious MT with migration into the hindgut. Triatomines ingest blood from a variety of mammals, and quickly begin processing the blood meal. MT are flushed from the hindgut during the defecation process and are capable of initiating host infection through breaks in the skin (i.e., the insect bite site), or by entry through mucosal routes such as the eyes or mouth. Once inside the cell, MT differentiate into amastigotes (AMA) which are the only dividing parasite form present in humans. After several rounds of division, AMA differentiate into blood-form trypomastigotes (BFT) which are released upon cell lysis. These BFT can infect local cells, other cells in the body after dissemination through the circulation, or new insects. Proteins expressed in parasite life stages relevant for human infection (MT, AMA, and BFT) are worth consideration as potential targets of vaccine-induced immunity in humans and other susceptible mammals.

Immunity to *T. cruzi* infection is multifaceted involving a variety of cell types. *T. cruzi* infection induces robust B cell (antibody) responses in both mice and humans. However, antibody secreting B cells may provide more important effects for prevention of $CD8^+$ T cell exhaustion during chronic *T. cruzi* infection as the inventors have recently described (Sullivan et al., 2015). Both $CD4^+$ and $CD8^+$ T cells are critical in the development of protective immunity (Tarleton, 1990; Tarleton, 1990; Wizel et al., 1997 and Wizel et al., 1997). The inventors recently demonstrated that dendritic cell vaccines pulsed with only a single $CD4^+$ T cell epitope and a single $CD8^+$ T cell epitope from the *T. cruzi* trans-sialidase can protect mice against highly virulent *T. cruzi* challenge (manuscript submitted). $CD4^+$ T cells are important in the priming of parasite-specific immunity, whereas $CD8^+$ T cells are essential for effector function and parasite clearance. Once immunity is generated, $CD8^+$ T cells alone can protect mice against parasite challenge as shown in adoptive transfer experiments (Eickhoff et al., 2011). In humans infected with *T. cruzi*, vigorous $CD8^+$ T cell responses have been reported (Laucella et al., 2004; Laucella et al., 2009 and Lasso et al., 2010). Furthermore, frequencies of parasite-specific $CD8^+$ IFN-γ-producing T cells inversely correlate with severity of Chagas disease progression (Laucella et al., 2004). Therefore, it is essential that vaccines target the induction of $CD8^+$ T cell responses to offer optimal protective immunity.

The overwhelming majority of studies investigating immunity to *T. cruzi* infection are performed in mice, allowing clear cut answers to basic science questions, but not always relevant for human *T. cruzi* infection. T cell responses are not only species specific, but also MHC allele specific. Thus the specific peptides immunogenic in one mouse strain will likely not be immunogenic in other strains of mice or humans. Transgenic mice expressing human MHC (human leukocyte antigen; HLA) are useful tools for identifying T cell epitopes relevant for humans. Approximately 50% of humans express MHC class I alleles which share similar binding profiles and belong to the HLA-A2 supertype (Reche & Reinherz, 2005). T cell epitopes immunogenic in HLA-A2 transgenic mice therefore have a high likelihood of being immunogenic in many humans. Thus, the ability to identify HLA-A2 restricted $CD8^+$ T cell epitopes immunogenic in HLA-A2 transgenic mice would greatly assist translational Chagas vaccine development efforts.

SUMMARY

Thus, in accordance with the present disclosure, there is provided a peptide comprising an amino acid sequence selected from the group consisting of SEQ ID NO: 1-5 and 7-30, or a peptide composition comprising at least two peptides comprising an amino acid sequence selected from the group consisting of SEQ ID NO: 1-5 and 7-30. The peptide may individually be 9-15 residues in length. The peptide may be fused to another amino acid sequence. The peptide may be formulated in a pharmaceutically acceptable buffer, diluent or excipient, or is lyophilized.

Also provided is a method of inducing an immune response in a subject comprising administering to a subject one or more peptides comprising an amino acid sequence selected from the group consisting of SEQ ID NO: 1-5 and 7-30. The peptide or peptides may individually be selected from 9-15 residues in length. The peptide or peptides may be fused to another amino acid sequence. The method may provide that at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 distinct peptides are administered to said subject, or wherein said peptide composition comprises 3, 4, 5, 6, 7, 8, 9, 10, 11, 12, 13, 14, 15, 16, 17, 18, 19, 20, 21, 22, 23, 24, 25, 26, 27, 28, 29, or 30 distinct peptides. The method may further comprise inducing an immune response to a peptide comprising SEQ ID NO: 6.

The at least one trans-sialidase peptide and one non-trans-sialidase peptide may be administered; or at least one functional trans-sialidase peptide and at least one non-functional trans-sialidase peptide may be administered; or at least one functional trans-sialidase peptide and at least one non-trans-sialidase peptide may be administered; or at least one non-functional trans-sialidase peptide and at least one non-trans-sialidase peptide may be administered. The non-trans-sialidase protein may be selected from the group consisting of cruzipain precursor, surface protease GP63, histone H3, ATP synthase, citrate synthase, pitrilysin-like metalloprotease, retrotransposon host spot protein, HSP70, surafe protein ToIT, dynein light chain, pumilio/PUR RNA binding protein, and mucin-asociated surface protein.

The method may further comprise multiple administrations, and/or may comprises injection, such as subcutaneous, intradermal or intramuscular injection, and/or may comprises administration with an adjuvant, such as a squalene adjuvant, a cytokine adjuvant, a lipid adjuvant or a TLR ligand, and/or may comprise administering a total amount of peptide of between 50 μg/kg and 1 mg/kg. The subject may be is a human subject or non-human subject, such as a mouse. The method may further comprise measuring a CD8$^+$ T cell response in said subject following administration.

A vaccine formulation comprising one or more peptides comprising an amino acid sequence selected from the group consisting of SEQ ID NO: 1-5 and 7-30. The formulation may compress two or more peptides selected from the group consisting of SEQ ID NO: 1-5 and 7-30 fused together. The peptide or peptides is/are individually 9-15 residues in length. The peptide or peptides may be fused to a non-$T.$ $cruzii$ amino acid sequence. The formulation comprise at least 2, 3, 4, 5, 6, 7, 8, 9, 10, 11, 12, 13, 14, 15, 16, 17, 18, 19, 20, 21, 22, 23, 24, 25, 26, 27, 28, 29 or 30 distinct peptides. The formulation may further comprise a peptide having the sequence of SEQ ID NO: 6.

The formulation may comprise at least one peptide trans-sialidase peptide and one non-trans-sialidase peptide; may comprise at least one functional trans-sialidase peptide and at least one non-functional trans-sialidase peptide; may comprise at least one functional trans-sialidase peptide and at least one non-trans-sialidase peptide; or may comprise at least one non-functional trans-sialidase peptide and at least one non-trans-sialidase peptide. The formulation may comprise an adjuvant, such as a squalene adjuvant, a cytokine adjuvant, a lipid adjuvant or a TLR ligand. The formulation may be a liquid formulation, such as a liquid formulation in a pharmaceutically acceptable buffer, carrier or diluent, such as an injectable formulation. The formulation may be provided in a unit dosage of between 50 μg/kg and 1 mg/kg of said peptide(s). The formulation may be lyophilized.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-B—Immunoinformatic strategy for identification of HLA-A2-restricted CD8+ T cell epitopes from $T.$ $cruzi$. Genomic and proteomic data from TriTrypDB[25] was mined in order to identify HLA-restricted T cell epitopes in the highly conserved functional (enzymatically active) TS family (F-TS) and the more diverse non-functional TS family (NF-TS), or within other antigens expressed in parasite life stages relevant for human immunity (Non-TS). Conservation and epitope prediction analyses were performed using Conservatrix and EpiMatrix, respectively, in order to identify relatively conserved HLA-A2 binders in F-TS and NF-TS gene family members (FIG. 1A). Potentially secreted $T.$ $cruzi$ proteins shown to be expressed by mass spectrometry in amastigote (AMA), insect-borne infectious metacyclic trypomastigote (MT) and blood form trypomastigote (BFT) equivalent life stages were identified and EpiMatrix utilized to predict HLA-A2 binding peptides (Non-TS genes; FIG. 1B).

FIGS. 2A-C—Immunogenicity of predicted HLA-A2 restricted $T.$ $cruzi$ epitopes. HLA-A2 transgenic mice were vaccinated twice, two weeks apart with mature dendritic cells pulsed with functional TS (F-TS; FIG. 2A), Non-functional TS (NF-TS; FIG. 2B), or whole genome derived Non-TS peptide pools (FIG. 2C). One month later, CD8$^+$ T cells were isolated from control DC or peptide-pool pulsed DC vaccinated mice and stimulated overnight with APCs pulsed with individual F-TS, NF-TS, or Non-TS peptides in IFN-γ ELISPOT assays. Shown are mean±SE from representative experiments expressed as IFN-γ spot forming cells (SFC) per million CD8$^+$ T cells above DMSO control. Asterisks denote immunogenic peptides defined as responses greater than the mean+2 SE of all control CD8$^+$ T cell responses.

DESCRIPTION OF ILLUSTRATIVE EMBODIMENTS

Chagas disease is a major neglected tropical disease caused by persistent chronic infection with the protozoan parasite *Trypanosoma cruzi*. An estimated 11 million people are infected with *T. cruzi*, however only two drugs are approved for treatment and no vaccines are available. Thus there is an urgent need to develop vaccines and new drugs to prevent and treat Chagas disease. In this work, the inventors utilized immunoinformatic tools to identify T cell targets relevant for human infection with *T. cruzi*. The trans-sialidase (TS) gene family is a large family of homologous genes within the *T. cruzi* genome encoding over 1,400 members. There are 12 highly conserved TS gene family members which encode enzymatically active functional TS (F-TS), while the remaining TS family genes are less conserved, enzymatically inactive and have been hypothesized to be involved in immune evasion (non-functional TS; NF-TS). The inventors utilized a variety of immunoinformatic tools to identify HLA-A2 restricted $CD8^+$ T cell epitopes conserved within F-TS family members and NF-TS gene family members. They also utilized a whole-genome approach to identify T cell epitopes present within genes which have previously been shown to be expressed in life stages relevant for human infection (Non-TS genes). Thirty new immunogenic HLA-A2-restricted $CD8^+$ T cell epitopes were identified using IFN-γ ELISPOT assays after vaccination of humanized HLA-A2 transgenic mice with mature dendritic cells pulsed with F-TS, NF-TS, and Non-TS peptide pools. The immunogenic HLA-A2 restricted T cell epitopes identified in this work may serve as potential components of an epitope-based T cell targeted vaccine for Chagas disease.

These and other aspects of the disclosure are described in detail below.

I. DEFINITIONS

The phrases "isolated" or "biologically pure" refer to material which is substantially or essentially free from components which normally accompany the material as it is found in its native state. Thus, isolated peptides in accordance with the disclosure preferably do not contain materials normally associated with the peptides in their in situ environment.

An "epitope," also known as an antigenic determinant, is the part of a macromolecule that is recognized by the immune system, specifically by antibodies, B cells, or T cells.

"Major histocompatibility complex" or "MHC" is a cluster of genes that plays a role in control of the cellular interactions responsible for physiologic immune responses. In humans, the MHC complex is also known as the HLA complex. For a detailed description of the MHC and HLA complexes (see Paul, 1993).

"Human leukocyte antigen" or "HLA" is a human class I or class II major histocompatibility complex (MHC) protein (see, e.g., Stites, 1994).

An "HLA supertype or family," as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like supertype molecules (where xx denotes a particular HLA type), are synonyms.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "supermotif" is a peptide binding specificity shared by HLA molecules encoded by two or more HLA alleles. Thus, a preferably is recognized with high or intermediate affinity (as defined herein) by two or more HLA antigens.

"Cross-reactive binding" indicates that a peptide is bound by more than one HLA molecule; a synonym is degenerate binding.

A "protective immune response" refers to a T cell response to an antigen derived from an infectious agent, which prevents or at least partially arrests disease symptoms or infection. The immune response may also include an antibody response which has been facilitated by the stimulation of helper T cells.

II. CHAGAS DISEASE

A. Background

Chagas disease, or American trypanosomiasis, is a tropical parasitic disease caused by the protozoan *Trypanosoma cruzi*. It is spread mostly by insects known as triatominae or kissing bugs. The symptoms change over the course of the infection. In the early stage, symptoms are typically either not present or mild and may include fever, swollen lymph nodes, headaches, or local swelling at the site of the bite. After 8-12 weeks, individuals enter the chronic phase of disease and in 60-70% it never produces further symptoms. The other 30 to 40% of people develop further symptoms 10 to 30 years after the initial infection, including enlargement of the ventricles of the heart in 20 to 30%, leading to heart failure. An enlarged esophagus or an enlarged colon may also occur in 10% of people.

*T. cruzi* is commonly spread to humans and other mammals by the blood-sucking "kissing bugs" of the subfamily Triatominae. These insects are known by a number of local names, including: vinchuca in Argentina, Bolivia, Chile and Paraguay, barbeiro (the barber) in Brazil, pito in Colombia, chinche in Central America, and chipo in Venezuela. The disease may also be spread through blood transfusion, organ transplantation, eating food contaminated with the parasites, and by vertical transmission (from a mother to her fetus). Diagnosis of early disease is by finding the parasite in the blood using a microscope. Chronic disease is diagnosed by finding antibodies for *T. cruzi* in the blood.

Prevention mostly involves eliminating kissing bugs and avoiding their bites. Other preventative efforts include screening blood used for transfusions. A vaccine has not been developed as of 2013. Early infections are treatable with the medication benznidazole or nifurtimox. Medication nearly always results in a cure if given early, but becomes less effective the longer a person has had Chagas disease. When used in chronic disease, medication may delay or prevent the development of end-stage symptoms. Benznidazole and nifurtimox cause temporary side effects in up to 40% of people including skin disorders, brain toxicity, and digestive system irritation.

It is estimated that 7 to 8 million people, mostly in Mexico, Central America and South America, have Chagas disease as of 2013. In 2006, Chagas was estimated to result in 12,500 deaths per year. Most people with the disease are poor, and most people with the disease do not realize they are infected. Large-scale population movements have increased the areas where Chagas disease is found and these include many European countries and the United States. These areas have also seen an increase in the years up to 2014. The disease was first described in 1909 by Carlos Chagas after whom it is named. It affects more than 150 other animals.

B. *T. cruzi*

The *Trypanosoma cruzi* life cycle starts in an animal reservoir, usually mammals, wild or domestic, including humans. A triatomine bug serves as the vector. While taking a blood meal, it ingests *T. cruzi*. In the triatomine bug (*Triatoma infestans*) the parasite goes into the epimastigote stage, making it possible to reproduce. After reproducing through binary fission, the epimastigotes move onto the rectal cell wall, where they become infectious. Infectious *T. cruzi* are called metacyclic trypomastigotes. When the triatomine bug subsequently takes a blood meal from a human, it defecates. The trypomastigotes are in the feces and are capable of swimming into the host's cells using flagella, a characteristic swimming tail dominant in the Euglenoid class of protists.

The trypomastigotes enter the human host through the bite wound or by crossing mucous membranes. The host cells contain macromolecules such as laminin, thrombospondin, heparin sulphate, and fibronectin that cover their surface. These macromolecules are essential for adhesion between parasite and host and for the process of host invasion by the parasite. The trypomastigotes must cross a network of proteins that line the exterior of the host cells in order to make contact and invade the host cells. The molecules and proteins on the cytoskeleton of the cell also bind to the surface of the parasite and initiate host invasion. When they enter a human cell, they become amastigotes. This is another reproductive stage. After reproducing through binary fission until a large amount of amastigotes is present in a cell, pseudocysts are formed there. The amastigotes then turn back into trypomastigotes, and the cell bursts. The trypomastigotes swim along to either infect other cells or get sucked up by other reduviid bugs.

C. Symptoms

The human disease occurs in two stages: an acute stage, which occurs shortly after an initial infection, and a chronic stage that develops over many years. The acute phase lasts for the first few weeks or months of infection. It usually occurs unnoticed because it is symptom-free or exhibits only mild symptoms that are not unique to Chagas disease. These can include fever, fatigue, body aches, muscle pain, headache, rash, loss of appetite, diarrhea, nausea, and vomiting. The signs on physical examination can include mild enlargement of the liver or spleen, swollen glands, and local swelling (a chagoma) where the parasite entered the body.

The most recognized marker of acute Chagas disease is called Romaña's sign, which includes swelling of the eyelids on the side of the face near the bite wound or where the bug feces were deposited or accidentally rubbed into the eye. Rarely, young children, or adults may die from the acute disease due to severe inflammation/infection of the heart muscle (myocarditis) or brain (meningoencephalitis). The acute phase also can be severe in people with weakened immune systems.

If symptoms develop during the acute phase, they usually resolve spontaneously within three to eight weeks in approximately 90% of individuals. Although the symptoms resolve, even with treatment the infection persists and enters a chronic phase. Of individuals with chronic Chagas disease, 60-80% will never develop symptoms (called indeterminate chronic Chagas disease), while the remaining 20-40% will develop life-threatening heart and/or digestive disorders during their lifetime (called determinate chronic Chagas disease). In 10% of individuals, the disease progresses directly from the acute form to a symptomatic clinical form of chronic Chagas disease.

The symptomatic (determinate) chronic stage affects the nervous system, digestive system and heart. About two-thirds of people with chronic symptoms have cardiac damage, including dilated cardiomyopathy, which causes heart rhythm abnormalities and may result in sudden death. About one-third of patients go on to develop digestive system damage, resulting in dilation of the digestive tract (megacolon and megaesophagus), accompanied by severe weight loss. Swallowing difficulties (secondary achalasia) may be the first symptom of digestive disturbances and may lead to malnutrition.

20% to 50% of individuals with intestinal involvement also exhibit cardiac involvement. Up to 10% of chronically infected individuals develop neuritis that results in altered tendon reflexes and sensory impairment. Isolated cases exhibit central nervous system involvement, including dementia, confusion, chronic encephalopathy and sensory and motor deficits.

The clinical manifestations of Chagas disease are due to cell death in the target tissues that occurs during the infective cycle, by sequentially inducing an inflammatory response, cellular lesions, and fibrosis. For example, intracellular amastigotes destroy the intramural neurons of the autonomic nervous system in the intestine and heart, leading to mega-intestine and heart aneurysms, respectively. If left untreated, Chagas disease can be fatal, in most cases due to heart muscle damage.

D. Transmission

In Chagas-endemic areas, the main mode of transmission is through an insect vector called a triatomine bug. A triatomine becomes infected with *T. cruzi* by feeding on the blood of an infected person or animal. During the day, triatomines hide in crevices in the walls and roofs.

The bugs emerge at night, when the inhabitants are sleeping. Because they tend to feed on people's faces, triatomine bugs are also known as "kissing bugs". After they bite and ingest blood, they defecate on the person. Triatomines pass *T. cruzi* parasites (called trypomastigotes) in feces left near the site of the bite wound.

Scratching the site of the bite causes the trypomastigotes to enter the host through the wound, or through intact mucous membranes, such as the conjunctiva. Once inside the host, the trypomastigotes invade cells, where they differentiate into intracellular amastigotes. The amastigotes multiply by binary fission and differentiate into trypomastigotes, which are then released into the bloodstream. This cycle is repeated in each newly infected cell. Replication resumes only when the parasites enter another cell or are ingested by another vector.

Dense vegetation (such as that of tropical rainforests) and urban habitats are not ideal for the establishment of the human transmission cycle. However, in regions where the sylvatic habitat and its fauna are thinned by economic exploitation and human habitation, such as in newly deforested areas, piassava palm culture areas, and some parts of the Amazon region, a human transmission cycle may develop as the insects search for new food sources.

*T. cruzi* can also be transmitted through blood transfusions. With the exception of blood derivatives (such as fractionated antibodies), all blood components are infective.

The parasite remains viable at 4° C. for at least 18 days or up to 250 days when kept at room temperature. It is unclear whether *T. cruzi* can be transmitted through frozen-thawed blood components.

Other modes of transmission include organ transplantation, through breast milk, and by accidental laboratory exposure. Chagas disease can also be spread congenitally (from a pregnant woman to her baby) through the placenta, and accounts for approximately 13% of stillborn deaths in parts of Brazil.

E. Diagnosis

The presence of *T. cruzi* is diagnostic of Chagas disease. It can be detected by microscopic examination of fresh anticoagulated blood, or its buffy coat, for motile parasites; or by preparation of thin and thick blood smears stained with Giemsa, for direct visualization of parasites. Microscopically, *T. cruzi* can be confused with *Trypanosoma rangeli*, which is not known to be pathogenic in humans. Isolation of *T. cruzi* can occur by inoculation into mice, by culture in specialized media (for example, NNN, LIT); and by xenodiagnosis, where uninfected Reduviidae bugs are fed on the patient's blood, and their gut contents examined for parasites.

Various immunoassays for *T. cruzi* are available and can be used to distinguish among strains (zymodemes of *T. cruzi* with divergent pathogenicities). These tests include: detecting complement fixation, indirect hemagglutination, indirect fluorescence assays, radioimmunoassays, and ELISA. Alternatively, diagnosis and strain identification can be made using polymerase chain reaction (PCR).

F. Prevention

There is currently no vaccine against Chagas disease. Prevention is generally focused on decreasing the numbers of the insect that spreads it (*Triatoma*) and decreasing their contact with humans. This is done by using sprays and paints containing insecticides (synthetic pyrethroids), and improving housing and sanitary conditions in rural areas. For urban dwellers, spending vacations and camping out in the wilderness or sleeping at hostels or mud houses in endemic areas can be dangerous; a mosquito net is recommended. Some measures of vector control include:

A yeast trap can be used for monitoring infestations of certain species of triatomine bugs (*Triatoma sordida, Triatoma brasiliensis, Triatoma pseudomaculata*, and *Panstrongylus megistus*).

Promising results were gained with the treatment of vector habitats with the fungus *Beauveria bassiana*. Targeting the symbionts of Triatominae through paratransgenesis can also be performed.

A number of potential vaccines are currently being tested. Vaccination with *Trypanosoma rangeli* has produced positive results in animal models. More recently, the potential of DNA vaccines for immunotherapy of acute and chronic Chagas disease is being tested by several research groups.

Blood transfusion was formerly the second-most common mode of transmission for Chagas disease, but the development and implementation of blood bank screening tests has dramatically reduced this risk in the 21st century. Blood donations in all endemic Latin American countries undergo Chagas screening, and testing is expanding in countries, such as France, Spain and the United States, that have significant or growing populations of immigrants from endemic areas. In Spain, donors are evaluated with a questionnaire to identify individuals at risk of Chagas exposure for screening tests.

The US FDA has approved two Chagas tests, including one approved in April 2010, and has published guidelines that recommend testing of all donated blood and tissue products. While these tests are not required in U.S., an estimated 75-90% of the blood supply is currently tested for Chagas, including all units collected by the American Red Cross, which accounts for 40% of the U.S. blood supply. The Chagas Biovigilance Network reports current incidents of Chagas-positive blood products in the United States, as reported by labs using the screening test approved by the FDA in 2007.

G. Treatment

There are two approaches to treating Chagas disease, antiparasitic treatment, to kill the parasite; and symptomatic treatment, to manage the symptoms and signs of the infection. Management uniquely involves addressing selective incremental failure of the parasympathetic nervous system. Autonomic disease imparted by Chagas may eventually result in megaesophagus, megacolon and accelerated dilated cardiomyopathy. The mechanisms that explain why Chagas targets the parasympathetic autonomic nervous system, and spares the sympathetic autonomic nervous system, remain poorly understood.

1. Medication

Antiparasitic treatment is most effective early in the course of infection, but is not limited to cases in the acute phase. Drugs of choice include azole or nitro derivatives, such as benznidazole or nifurtimox. Both agents are limited in their capacity to effect parasitologic cure (a complete elimination of *T. cruzi* from the body), especially in chronically infected patients, and resistance to these drugs has been reported.

Studies suggest antiparasitic treatment leads to parasitological cure in about 60-85% of adults and more than 90% of infants treated in the first year of acute phase Chagas disease. Children (aged six to 12 years) with chronic disease have a cure rate of about 60% with benznidazole. While the rate of cure declines the longer an adult has been infected with Chagas, treatment with benznidazole has been shown to slow the onset of heart disease in adults with chronic Chagas infections.

Treatment of chronic infection in women prior to or during pregnancy does not appear to reduce the probability the disease will be passed on to the infant. Likewise, it is unclear whether prophylactic treatment of chronic infection is beneficial in persons who will undergo immunosuppression (for example, organ transplant recipients) or in persons who are already immunosuppressed (for example, those with HIV infection).

2. Complications

In the chronic stage, treatment involves managing the clinical manifestations of the disease. For example, pacemakers and medications for irregular heartbeats, such as the anti-arrhythmia drug amiodarone, may be life saving for some patients with chronic cardiac disease, while surgery may be required for megaintestine. Advanced disease cannot be reversed by parasitologic treatment once severe pathology occurs. Chronic heart disease caused by Chagas disease is now a common reason for heart transplantation surgery. Until recently, however, Chagas disease was considered a contraindication for the procedure, since the heart damage could recur as the parasite was expected to seize the opportunity provided by the immunosuppression that follows surgery.

It was noted that survival rates in Chagas patients could be significantly improved by using lower dosages of the immunosuppressant drug cyclosporin.

III. CHAGAS DISEASE PEPTIDES

A. Chagas Disease Proteins

Peptides for use in accordance with the present disclosure include a variety of functional and non-functional Chagas Disease gene products. Of particular interest is the Chagas Disease trans-sialidase (TS) protein. TS transfers sialic acid from host cells onto the parasite surface, a process known to be important in parasite infectivity. Other *T. cruzii* proteins of interest include mucin-associated surface proteins (MASP), gp63 surface proteases, cruzipain precursors, and pitrilysin-like metalloproteases, as well as other proteins mentioned in Table 1.

B. Peptide Compositions

As used herein, an "antigenic composition" comprises a Chagas Disease peptide antigen. Of particular interest here are peptides from the trans-sialidase peptide, and conserved epitopes therein. However, the other Chagas Disease peptides, discussed above, also are contemplated. In particular embodiments, the antigenic composition comprises or encodes one or more peptides comprising one or more sequences shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30, or an immunologically functional equivalent thereof. These sequences are shown in tabular form below in Table 1.

As used herein, an "amino acid" or "amino acid residue" refers to any naturally-occurring amino acid, any amino acid derivative or any amino acid mimic known in the art, including modified or unusual amino acids. In certain embodiments, the natural residues of the peptide are sequential, without any non-amino acid interrupting the sequence of natural amino acid residues. In other embodiments, the sequence may comprise one or more non-natural amino acid moieties.

The term "peptide" is used interchangeably with "oligopeptide" in the present specification to designate a series of residues, typically L-amino acids, connected one to the other, typically by peptide bonds between the α-amino and carboxyl groups of adjacent amino acids. Particular T cell-inducing oligopeptides of the disclosure are 15 residues or less in length and usually consist of between about 8 and about 13 residues, particularly 9 to 11 residues. Specific lengths of 9, 10, 11, 12, 13, 14 and 15 residues are contemplated.

An "immunogenic peptide" or "peptide epitope" is a peptide which comprises an allele-specific motif or supermotif such that the peptide will bind an HLA molecule and induce a T cell response. Thus, immunogenic peptides of the disclosure are capable of binding to an appropriate HLA molecule and thereafter inducing a T cell response to the antigen from which the immunogenic peptide is derived.

Modified or unusual amino acids include, but are not limited to, those shown on Table 2 below.

TABLE 1

Immunogenic HLA-A2 restricted $CD8^+$ T cell epitopes (SEQ ID NOS: 1-30, top to bottom)

| Peptide ID | Sequence | Protein or Family |
|---|---|---|
| F-TS-2 | EVYSLVFARL | F-TS family |
| NF-TS-2 | NVLLYNRPL | NF-TS gene family |
| NF-TS-3 | WLTDNTHIV | NF-TS gene family |
| NF-TS-4 | NTWRDEYLGV | NF-TS gene family |
| NF-TS-5 | KVGSDVFAV | NF-TS gene family |
| NF-TS-6 | RVFTSAVLL | NF-TS gene family |
| Non-TS 2 | VVMACLVPA | cruzipain precurser |
| Non-TS 3 | TLLFQVLLL | surface protease GP63 |
| Non-TS 4 | RIGDVCAEV | surface protease GP63 |
| Non-TS 5 | LLFQVLLLC | surface protease GP63 |
| Non-TS 6 | YVVSLLADT | histone H3 |
| Non-TS 7 | ALHSLVLFL | hypothetical protein |
| Non-TS 8 | AVIPSTFPL | ATP synthase |
| Non-TS 9 | SLFPFFFFV | hypothetical protein |
| Non-TS 10 | FLVDTIYSI | citrate synthase |
| Non-TS 11 | YLDAVFYPL | pitrilysin-like metalloprotease |
| Non-TS 12 | SLLCVISFI | retrotransposon hot spot protein |
| Non-TS 13 | ALLPWLLVL | hypothetical protein |
| Non-TS 16 | LMNDVWFSL | heat shock protein 70 |
| Non-TS 17 | FLIFRFMVL | hypothetical protein |
| Non-TS 18 | FMACHTNPI | hypothetical protein |
| Non-TS 19 | MMHPFLCAL | surface protein TolT |
| Non-TS 24 | SMNAGLYLL | retrotransposon hot spot protein |
| Non-TS 25 | AVFDSVYSV | surface protease GP63 |
| Non-TS 26 | FLNQFGTRL | hypothetical protein |
| Non-TS 27 | SMQEYRHMV | dynein light chain |
| Non-TS 29 | SVVSVFFLL | histone H3 |
| Non-TS 31 | QMLHNVASL | pumilio/PUF RNA binding protein |
| Non-TS 32 | MMMTGRVLL | mucin-associated surface protein |
| Non-TS 33 | TLMDFCPYI | surface protease GP63 |

TABLE 2

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | 2-alanine, -Amino-propionic acid | Ahyl | Allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | Allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In particular embodiments, biocompatible protein, polypeptide or peptide containing compositions will generally be mammalian proteins or peptides or synthetic proteins or peptides each essentially free from toxins, pathogens and harmful immunogens.

C. Variants

The present disclosure also contemplates modification of the peptides shown in Table 1. Such peptide "variants" may include additional residues, such as additional N- or C-terminal amino acids, or altered/substituted/modified amino acids, and yet still comprise one of the sequences disclosed herein, so long as the sequence meets the criteria set forth above, including the maintenance of biological activity.

The following is a discussion based upon changing the amino acids of a peptide to create a variant peptide. In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

A specialized kind of insertional variant is the fusion protein. This molecule generally has all or a substantial portion of the native molecule, linked at the N- or C-terminus, to all or a portion of a second peptide or polypeptide. In particular, embodiments where multiple peptides of the present disclosure (SEQ ID NOS:1-30) are linked in a "head-to-tail" fashion to create a polytope molecule, i.e., an epitope multimer. The peptides may be linked to each directly though peptide bonds, or they may be separated by peptide "spacers," or they may be attached using non-peptide or peptoid "linker," which are well known in the art. In addition, inclusion of a cleavage site at or near the fusion junction or linker will facilitate removal or release of other peptide sequences. Other useful fusions include linking of functional domains, such as active sites from enzymes such as a hydrolase, glycosylation domains, cellular targeting signals or transmembrane regions.

D. Peptide Synthesis and Purification

The peptides of the present disclosure can be synthesized in solution or on a solid support in accordance with conventional techniques. Various automatic synthesizers are commercially available and can be used in accordance with known protocols. See, for example, Stewart & Young (1984); Tam et al. (1983); Merrifield (1986); and Barany & Merrifield (1979), Houghten et al. (1985). In some embodiments, peptide synthesis is contemplated by using automated peptide synthesis machines, such as those available from Applied Biosystems (Foster City, Calif.). The peptides of the present disclosure may be isolated and extensively dialyzed to remove undesired small molecular weight molecules and/or lyophilized for more ready formulation into a desired vehicle.

In certain embodiments the peptides of the present disclosure may be purified. The term "purified peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein/peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an HLA-restricted peptide of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. Although this preparation will be purified in an inactive form, the denatured material will still be capable of transducing cells. Once inside of the target cell or tissue, it is generally accepted that the polypeptide will regain full biological activity.

As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

IV. VACCINE PROTOCOLS AND FORMULATIONS

In an embodiment of the present disclosure, a method of treatment and prevention of Chagas Disease by the delivery of a peptide or peptide composition is contemplated. An effective amount of the vaccine composition, generally, is defined as that amount sufficient to detectably and repeatedly ameliorate, reduce, minimize or limit the extent of the disease or condition or symptoms thereof. More rigorous definitions may apply, including elimination, eradication or cure of disease.

A. Administration

The peptides of the present disclosure may be used in vivo to produce anti-Chagas Disease immune response, and thus constitute therapeutic and prophylactic vaccines. Thus, the peptides can be formulated for parenteral administration, e.g., formulated for injection via the intradermal, intravenous, intramuscular, subcutaneous, or intraperitoneal routes. Administration by the intradermal and intramuscular routes are specifically contemplated. The vaccine can also be administered by a topical route directly to the mucosa, for example by nasal drops or mist, inhalation, or by nebulizer.

Some variation in dosage and regimen will necessarily occur depending on the age and medical condition of the subject being treated, as well as the route chosen. The person responsible for administration will, in any event, determine the appropriate dose for the individual subject. In many instances, it will be desirable to have multiple administrations of the vaccine. Thus, the compositions of the disclosure may be administered 1, 2, 3, 4, 5, 6, 7, 8, 9, 10, or more times. The administrations will normally be at from one to twelve week intervals, more usually from one to six week intervals. Periodic re-administration will be desirable with recurrent exposure to the pathogen.

The administration may use various "unit doses." Unit dose is defined as containing a predetermined-quantity of the therapeutic composition. The quantity to be administered, and the particular route and formulation, are within the skill of those in the clinical arts.

B. Measuring Immune Responses

One of ordinary skill would know various assays to determine whether an immune response against a peptide was generated. The phrase "immune response" includes both cellular and humoral immune responses. Various B lymphocyte and T lymphocyte assays are well known, such as ELISAs, cytotoxic T lymphocyte (CTL) assays, such as chromium release assays, proliferation assays using peripheral blood lymphocytes (PBL), tetramer assays, and cytokine production assays. See Benjamini et al. (1991), hereby incorporated by reference.

C. Injectable Formulations

One method for the delivery of a pharmaceutical according to the present disclosure is via injection. However, the pharmaceutical compositions disclosed herein may alternatively be administered intravenously, intradermally, intramuscularly, or even intraperitoneally as described in U.S. Pat. Nos. 5,543,158; 5,641,515 and 5,399,363 (each specifically incorporated herein by reference in its entirety).

Injection may be by syringe or any other method used for injection of a solution, as long as the agent can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. Sterile aqueous media that can be employed will be known to those of skill in the art in light of the present disclosure. For example, one dosage may be dissolved in 1 ml of isotonic NaCl solution and either added to 1000 ml of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous injectable composition that contains a protein as an active ingredient is well understood in the art.

D. Additional Vaccine Components

In other embodiments of the disclosure, the antigenic composition may comprise an additional immunostimulatory agent. Immunostimulatory agents include but are not limited to additional antigens, an immunomodulator, an antigen presenting cell or an adjuvant. In other embodiments, one or more of the additional agent(s) is covalently bonded to the antigen or an immunostimulatory agent, in any combination.

1. Adjuvants

As also well known in the art, the immunogenicity of a particular immunogen composition can be enhanced by the use of non-specific stimulators of the immune response, known as adjuvants. Adjuvants have been used experimentally to promote a generalized increase in immunity against antigens (e.g., U.S. Pat. No. 4,877,611). Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. Suitable molecule adjuvants include all acceptable immunostimulatory compounds, such as cytokines, toxins or synthetic compositions.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant. Other adjuvants that may also be used include IL-1, IL-2, IL-4, IL-7, IL-12, γ-interferon, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made by aggregation of the antigen in the vaccine by heat treatment with temperatures ranging between about 70° to about 101° C. for a 30 second to 2-minute period, respectively. Aggregation by reactivating with pepsin-treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen. Derivatives of muramyl dipeptide, such as the amino acid derivative threonyl-MDP, and the fatty acid derivative MTPPE, are also contemplated.

In certain embodiments, hemocyanins and hemoerythrins may also be used in the disclosure. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is believed to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present disclosure.

BCG (*bacillus* Calmette-Guerin, an attenuated strain of *Mycobacterium*) and BCG-cell wall skeleton (CWS) may also be used as adjuvants, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945. BCG is an important clinical tool because of its immunostimulatory properties. BCG acts to stimulate the reticulo-endothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Late et al., 1984). It is one of the few vaccines that can be given at birth, it engenders long-lived immune responses with only a single dose, and there is a worldwide distribution network with experience in BCG vaccination. An exemplary BCG vaccine is sold as TICE BCG (Organon Inc., West Orange, N.J.).

Amphipathic and surface active agents, e.g., saponin and derivatives such as QS21 (Cambridge Biotech), form yet another group of adjuvants for use with the immunogens of the present disclosure. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present disclosure.

Another group of adjuvants are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

Those of skill in the art will know the different kinds of adjuvants that can be conjugated to cellular vaccines in accordance with this disclosure and these include alkyl lysophosphilipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed in connection with the disclosure (Takada et al., 1995).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Adjuvants may be encoded by a nucleic acid (e.g., DNA or RNA). It is contemplated that such adjuvants may be also be encoded in a nucleic acid (e.g., an expression vector) encoding the antigen, or in a separate vector or other construct. Nucleic acids encoding the adjuvants can be delivered directly, such as for example with lipids or liposomes.

2. Biological Response Modifiers

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); low-dose Cyclophosphamide (CYP; 300 mg/m$^2$) (Johnson/Mead, N.J.), cytokines such as γ-interferon, IL-2, or IL-12 or genes encoding proteins involved in immune helper functions, such as B-7.

3. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-α, MIP1-β, IP-10 and combinations thereof. The skilled artisan will recognize that certain cytokines (e.g., IFN's) are also known to have chemoattractant effects and could also be classified under the term chemokines.

4. Immunogenic Carrier Proteins

The use of peptides for antibody generation or vaccination may requires conjugation of the peptide to an immunogenic carrier protein, such as hepatitis B surface antigen, keyhole limpet hemocyanin or bovine serum albumin. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine. Other immunopotentiating compounds are also contemplated for use with the compositions of the disclosure such as polysaccharides, including chitosan, which is described in U.S. Pat. No. 5,980,912, hereby incorporated by reference. Also, multiple (more than one) peptides may be crosslinked to one another (e.g., polymerized).

E. Combination Treatments

In certain embodiments, it may prove useful to use the vaccines of the present disclosure in conjunction with an anti-Chagas Disease therapy. Drugs of choice include azole or nitro derivatives, such as benznidazole or nifurtimox.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

As described above, the genome of *T. cruzi* contains multiple large gene families, and researchers have hypothesized that these gene families may have evolved as a mechanism of immune evasion (El Sayed et al., 2005). The largest *T. cruzi* gene family is the trans-sialidase (TS) gene family. TS transfers sialic acid from host cells onto the parasite surface—a process known to be important in parasite infectivity (Schenkman et al., 1994). While some studies have suggested the dampening of immunity by TS family proteins, the inventors and others have shown that TS antigens are highly immunogenic in both mice and humans (Eickhoff et al., 2011; Araujo et al., 2014 and Hoft et al., 2007). Immunization of multiple susceptible mouse strains with TS vaccines expressing enzymatically active (functional) TS antigens elicit robust T cell responses protective against highly lethal systemic *T. cruzi* challenges. TS gene family members are being pursued by multiple investigators as viable vaccine candidates; however, the most relevant T cell epitopes for human infection are unknown. One goal of this work was to identify T cell targets restricted by a major human MHC I supertype (HLA-A2) conserved within TS gene family members.

As shown in FIG. 1A, nearly half of the 1,430 TS gene family members are pseudogenes, and of the remaining 735 TS genes, only 12 encode proteins with enzymatic activity (El Sayed et al., 2005; Atwood et al., 2005 and Atwood et al., 2005). These 12 functional TS (F-TS) genes are highly homologous sharing 75% to over 90% sequence identity to the consensus *T. cruzi* TS enzyme sequence (GenBank accession D50685). Conversely, the 723 non-functional TS (NF-TS) genes are much more diverse largely of unknown function. In order to identify conserved T cell epitopes conserved within F-TS and NF-TS gene sets, the inventors employed a 2-staged approach using developmental tools developed by EpiVax. First, the Conservatrix algorithm parses all input proteins into individual 9-mers, then determines the number (conservation) of individual protein sequences within the input set which contain each specific 9-mer sequence (De Groot et al., 2009a). Sequences which were ≥50% conserved among the 12 F-TS genes or expressed by ≥5% of NF-TS genes were collected. Second, MHC-I binding predictions were performed on all of the 9-mer sequences parsed above using the matrix-based epitope prediction algorithm EpiMatrix (De Groot et al., 2009a; De Groot et al., 2009b and Moise et al., 2009). Briefly, EpiMatrix scores predict binding of all input sequences to 6 common human MHC-I alleles representing 6 major HLA supertypes which cover >95% of the population. EpiMatrix scores ≥1.64, representing the top 5% of peptides, have been shown to have a high likelihood to bind to the represented MHC-I supertype. Predicted HLA-A2 binding peptide sequences were checked for homology to known human sequences using BlastP, and the top 6 scoring HLA-A2 binders within the F-TS and NF-TS gene sets were chosen for further study.

In addition to identifying potential CD8+ T cell epitopes within F-TS and NF-TS gene family members, the inventors utilized a 'whole genome approach' to identify a more diverse set of T cell epitopes as shown in FIG. 1B. The genome and proteomes of all four major life stages of *T. cruzi* were analyzed in 2005, and data made available through the TriTrypDB (Aslett et al., 2010). The 2,185 genes expressed (mass spectrometry evidence) in life stages relevant for human infection (MT, AMA, and BFT) were gathered for analysis utilizing tools on the TriTrypDB. Since secreted proteins may be recognized better by the mammalian immune system because of increased delivery to the host cell cytoplasm, the inventors narrowed the strategy to include genes with predicted signal sequences but without multiple predicted trans-membrane domains or potential lipid attachment sites utilizing publicly available tools (TriTrypDB, LipoP, Phobias, SignalP). Each 9-mer frame was scored for predicted MHC I binding to six major supertypes using EpiMatrix as described above. 204 genes were analyzed in this manner, excluding TS sequences since these were included in the other gene set analyses. The inventors refer to epitopes predicted in this manner as Non-TS epitopes. This diverse set of epitopes included sequences from mucin-associated surface proteins (MASP), gp63 surface proteases, cruzipain precursors, pitrilysin-like metalloproteases, and others.

The inventors next developed a strategy involving peptide vaccination of HLA-A2 transgenic mice to identify immunogenic CD8+ T cell epitopes rather than performing MHC binding assays which do not confirm immunogenicity. All animal studies were conducted in AAALAC accredited facilities and were approved by the Saint Louis University Institutional Animal Care and Use Committee. HLA-A2 HHDII transgenic mice were provided by Ted Hansen (Washington University) with permission from Marion Berard at the Institut Pasteur and were bred and housed under pathogen-free conditions throughout the inventors' studies (Pascolo et al., 1997). These mice are devoid of normal murine MHC I expression, and express a chimeric HLA-A2 molecule consisting of human β2m and the α1-α2 domains of HLA-A2.1 fused to the α3 and cytoplasmic domains of H-2D$^b$(Pascolo et al., 1997). In order to prepare dendritic cells (DC) for use in peptide/DC vaccination experiments, 5×10$^6$ B16-Flt3L cells were i.p injected into 3-month old female HLA-A2 transgenic mice to induce expansion of immature DC as previously described (Pham et al., 2009). Two weeks later, DC were matured in vivo for 16-18 hours by intravenous injection of LPS (2 μg/mouse). Spleens were isolated and digested using collagenase and DNase, mechanically dispersed, processed to lyse red blood cells, and then CD11c+ cells were purified using magnetic beads following manufacturer guidelines (Miltenyi biotec). Mature DC (mDC) were suspended in complete DC media (2 parts fresh complete media plus 1 part B16-Flt3L conditioned media) supplemented with 1,000 U/ml GM-CSF, and pulsed with pools of F-TS, NF-TS, or Non-TS predicted HLA-A2 binders (JPT Peptide Technologies) at 5 μg/ml of each peptide for 2 hours. Mature DC were also pulsed with the known I-A$^b$-restricted CD4+ T cell epitope OVA323-339 to provide CD4+ T cell help for the development of CD8+ T cell responses. Mice were vaccinated twice, two weeks apart with 1×10$^6$ peptide-pulsed mDC intravenously.

Four weeks following the final vaccination, individual peptide-specific CD8+ T cell responses were studied using IFN-γ ELISPOT assays (Sullivan et al., 2011). Briefly, splenic CD8+ T cells were isolated from control and peptide-pulsed DC vaccinated mice using Miltenyi CD8 microbeads and added to IFN-γ ELISPOT assays (1×10$^5$ CD8+ T cells/well). Naïve total spleen cells were pulsed with individual peptides (5 μg/ml final concentration) and used as stimulator cells in these ELISPOT assays (3×10$^5$ per well). After overnight co-culture, IFN-γ ELISPOT plates were developed and spots enumerated as previously described (Sullivan et al., 2011). Shown in FIGS. 2A-C are results from these experiments. As expected, CD8+ T cells from mice vaccinated with control mDC did not respond to the predicted HLA-A2-restricted T cell epitopes. Many of the TS family and Non-TS predicted peptides elicited responses. The highly conserved functional TS family epitope F-TS-2 elicited the strongest response of any peptide studied in these assays (nearly 5,000 IFN-γ SFC/million CD8+ T cells; FIG. 2A). Several responses were elicited by stimulation of T cells from mice vaccinated with NF-TS peptides (5 of 6 NF-TS peptides were immunogenic; FIG. 2B). In addition, 24 Non-TS epitopes were found to be HLA-A2 restricted CD8+ T cell epitopes (FIG. 1B). In total, the inventors identified 30 new HLA-A2 restricted CD8+ T cell epitopes using a novel approach involving genomic, proteomic, and immunoinformatic analyses.

Previous studies aimed at CD8+ T cell epitope discovery in human-translatable models have focused on identifying T cell epitopes from either a single T. cruzi protein or a small number of similar T. cruzi genes. It has been postulated that T. cruzi has developed complicated mechanisms to evade host cell immunity allowing for parasite persistence. The TS superfamily with 1,430 gene members is significantly over-represented in the T. cruzi genome, however, the complexity of the TS superfamily and patterns of immune dominance of specific TS CD8+ T cell epitopes are not well understood (El Sayed et al., 2005; Atwood et al., 2005; Martin et al., 2006 and Rosenberg et al., 2010). The mechanism responsible for the evolution and expansion of the TS gene superfamily is not known. On the one hand, TS may dampen overall immunity through generation of altered peptide ligands, possibly contributing to parasite persistence (Plebanski et al., 1999). On the other hand, the inventors and others have shown that TS is highly immunogenic in both mice and humans, and TS as a vaccine candidate is as good or better at inducing protective immunity in mice than any antigen tested thus far. While there is little evidence to support the belief that large superfamilies in T. cruzi including TS have developed in order to evade host-cell mediated immunity, generating immunity to a diverse group of proteins using multi-epitope T cell targeted vaccines might prove to be a sensible tactic to circumvent these hypothesized parasite persistence strategies. The inventors have utilized a novel approach to identify T cell epitopes expressed by very diverse T. cruzi proteins. The immunogenic epitope sequences from F-TS, NF-TS, and Non-TS gene sets (shown in FIG. 2A0C and summarized in Table I) are encoded by genes with diverse functions. In this limited study, the inventros have identified T cell epitopes from enzymatically active as well as more diverse non-functional TS gene family members (6 total conserved immunogenic TS superfamily epitopes). In addition, they have identified 24 immunogenic HLA-A2 restricted epitopes from at least 13 different proteins using a modified whole-genome epitope identification approach. Future studies should investigate the relative levels of protective immunity induced by vaccination with conserved F-TS, NF-TS, and diverse Non-TS epitopes described here.

The HLA-A2 transgenic mice utilized in the studies above are extremely susceptible to T. cruzi infection. The $LD_{50}$ in this mouse strain is less than 100 parasites, even when using relatively non-virulent culture-derived metacyclic trypomastigotes (CMT) challenges (not shown). Although the inventors have been unable to induce long-term survival in naïve HLA-A2 transgenic animals after even low level parasite infection, vaccines encoding multiple CD8+ T cell epitopes may be able to confer some degree of protection in this mouse strain. Efforts to investigate protective immunity induced by multi-epitope CD8+ T cell targeted vaccines are ongoing. Liposomal-peptide formulations, naked DNA vaccines, adjuvanted recombinant protein, and attenuated viral vectors will be utilized to deliver multi-epitope antigens expressed in a single open reading frame (ORF). However, the optimal format, dose, and delivery routes are not well established. Futures studies investigating protective immunity induced by multi-epitope T cell targeted T. cruzi vaccines should give special attention to these details.

An HLA supertype is a group of genetically distinct HLA alleles which share similar peptide binding properties. Nine MHC class I supertypes have been identified (Sidney et al., 2008). However, >95% of individuals carry at least one HLA allele classified into one of six most common MHC I supertypes. An estimated 50% of individuals from wide-ranging backgrounds express the HLA-A2 supertype (Reche & Reinherz, 2005). In the current study, the inventors identified 30 diverse CD8+ T cell epitopes restricted by this major sypertype (A2). The logical extension of the work described above is to develop multi-epitope vaccines to induce protective immunity in diverse human populations. Therefore, additional CD8+ T cell epitopes restricted by the other HLA supertypes need to be identified. Similar strategies to those described in this report utilizing EpiMatrix prediction of F-TS, NF-TS, and Non-TS gene sets restricted by additional HLA supertypes should be employed to identify additional T cell epitopes relevant for diverse human populations. Long-term strategies to develop either customized vaccines based on an individual's HLA type or a master vaccine encoding different T cell epitopes restricted by all six major supertypes should be investigated. The optimal number of epitopes needed to cover all populations, as well as the optimal vaccine formulations (DNA, viral vector, adjuvanted recombinant protein) must be carefully studied.

It is well established that optimal CD8+ T cell responses are generated in the presence of robust CD4+ T cell help (Fujimura et al., 2001). CD4+ T cells are critical for the development of protective immunity against T. cruzi infection (Fujimura et al., 2001 and Fujimura et al., 2001). When normally protective T. cruzi vaccines are depleted of CD4+ T cell epitope regions they lose their protective capacities (Fujimura et al., 2001). Thus, new T cell-based T. cruzi vaccines should include immunogenic CD4+ T cell epitopes to help drive effective CD8+ T cell responses. MHC class II epitope prediction algorithms have been shown to be accurate, and more recently tools have been developed to identify clusters of pan DR-restricted class II epitopes (De Groot et al., 2009b and Moise et al., 2009). For example, matrix-based epitope prediction algorithms have been utilized to identify conserved variola/vaccinia CD4+ T cell epitopes that when formulated as multi-epitope vaccines were able to confer protection against lethal vaccinia challenges in humanized mice (Moise et al., 2009 and Moise et al., 2011). A similar strategy should be utilized to identify promiscuous CD4+ T cell epitopes (or T cell epitope clusters) within the F-TS, NF-TS, and Non-TS gene sets described in this report. Additionally, antigen-specific B cells have been shown to play a protective role in T. cruzi infection as both producers of lytic antibodies for extracellular parasites reducing overall parasite burden and as antigen presenting cells. Furthermore, the inventors have recently shown that T. cruzi specific B cells producing potent antibody responses can help prevent CD8+ T cell exhaustion (Sullivan et al., 2015). Recent efforts by several groups utilizing overlapping peptide arrays or high-throughput bioinformatic approaches have resulted in the identification of specific antibody epitopes in several T. cruzi genes (Bottino et al., 2013;

Mendes et al., 2013 and Balouz et al., 2015). A three-tiered approach focused on the inclusion of $CD4^+$ T helper epitopes, $CD8^+$ T cell epitopes, and B cell epitopes should be investigated for use as both prophylactic and therapeutic vaccines for the prevention and treatment of Chagas disease.

The results presented here represent the first mass-effort to identify $CD8^+$ T cell epitopes from diverse *T. cruzi* gene sets relevant for human infection. Many previous attempts aimed at identifying immunogenic $CD8^+$ T cell epitopes have utilized standard laboratory mouse strains expressing murine MHC (Fujimura et al., 2001 and Fujimura et al., 2001). While those results have helped elucidate much of what is known today about immunity to *T. cruzi* infection (including mechanisms of protection), the epitopes identified cannot be presented to human T cells by HLA. Here, the inventors have utilized a multifaceted approach to identify parasite proteins and their encoded T cell epitopes restricted by human MHC, specifically HLA-A2 which is expressed by nearly half of the human population. Thus, the $CD8^+$ T cell targets identified in this work are highly relevant for the development of effective vaccines to protect humans at risk of Chagas disease.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

U.S. Pat. No. 4,435,386
U.S. Pat. No. 4,436,727
U.S. Pat. No. 4,436,728
U.S. Pat. No. 4,505,899
U.S. Pat. No. 4,505,900
U.S. Pat. No. 4,520,019
U.S. Pat. No. 4,554,101
U.S. Pat. No. 4,579,945
U.S. Pat. No. 4,866,034
U.S. Pat. No. 4,877,611
U.S. Pat. No. 4,950,645
U.S. Pat. No. 5,399,363
U.S. Pat. No. 5,466,468
U.S. Pat. No. 5,543,158
U.S. Pat. No. 5,641,515
U.S. Pat. No. 5,846,233
U.S. Pat. No. 5,980,912
Apt et al., *Am J Trop Med Hyg.*, 59:133-8, 1998.
Araujo et al., *Mediators Inflamm.*, 2014:605023, 2014.
Aslett et al., *Nucleic Acids Res.*, 38:D457-62, 2010.
Atwood et al., *Science*, 309:473-6, 2005.
Azuma et al., *Cell Immunol.*, 116(1):123-134, 1988.
Balouz et al., *Clin Vaccine Immunol*, [INSERT] 2015.
Barany & Merrifield, In: The Peptides, Gross and Meienhofer (Eds.), Academic Press, NY, 1-284, 1979.
Benjamini et al., *Adv. Exp. Med. Biol.*, 303:71-77, 1991.
Bern & Montgomery, *Clin Infect Dis.*, 49:e52-e4, 2009.
Bottino et al., *BMC Infect Dis*, 13:568, 2013.
Brandariz et al., *Lancet*, 346:1370-1, 1995.
Capaldi et al., *Biochem. Biophys. Res. Comm.*, 74(2):425-433, 1977.
De Groot et al., *Clin Immunol.*, 131:189-201, 2009b.
De Groot et al., *Vaccine*, 27:5740-7, 2009a.
Eickhoff et al., *PLoS NTD*, 5: e983, 2011.
El Sayed et al., *Science*, 309:409-15, 2005.
Fujimura et al., *Infect Immun.*, 69:5477-86, 2001.
Hoft et al., *Infect Immun*, 68:197-204, 2000.
Hoft et al., *J Immunol.*, 179:6889-900, 2007.
Houghten et al., *Infect. Immun.*, 48(3):735-740, 1985.
Husson et al., *J Bacteriol.*, 172(2):519-524, 1990.
Jackson et al., *Clin Infect Dis.*, 51:e69-75, 2010.
Jacobs et al., *Nature*, 327(6122):532-535, 1987.
Kyte & Doolittle, *J Mol. Biol.*, 57(1):105-32, 1982.
Lasso et al., *Parasite Immunology*, 32:494-502, 2010.
Laucella et al., *Clin Infect Dis* 49:1675-84, 2009.
Laucella et al., *J Infect Dis.*, 189:909-18, 2004.
Lotte et al., *Adv. Tuberc. Res.*, 21:107-93; 194-245, 1984.
Luelmo, *Am. Rev. Respir. Dis.*, 125(3 Pt 2):70-72, 1982.
Marcon et al., *Memorias do Instituto Oswaldo Cruz*, 106:85-91, 2011.
Martin et al., *Nature*, 345(6277):739-743, 1990.
Martin et al., *PLoS Pathog*, 2:e77, 2006.
Mendes et al., *PLoS Negl Trop Dis*, 7:e2524, 2013.
Merrifield, *Science*, 232(4748):341-347, 1986.
Moise et al., *Vaccine*, 27:6471-9, 2009.
Moise et al., *Vaccine*, 29:501-11, 2011.
Pascolo et al., *J Exp Med.*, 185:2043-51, 1997.
Paul, *Transplant Proc.*, 25(2):2080-1, 1993.
PCT Appln. WO 91/16347
Pham et al., *J Immunol*, 183:2337-48, 2009.
Plebanski et al., *Nat Med*, 5:565-71, 1999.
Rabinovich et al., *Science*, 265(5177):1401-1404, 1994.
Rassi et al., *Lancet*, 375:1388-402, 2010.
Reche & Reinherz, *Nucleic Acids Res.*, 33:W138-42, 2005.
*Remington's Pharmaceutical Sciences*, 15$^{th}$ ed., pages 1035-1038 and 1570-1580, Mack Publishing Company, Easton, Pa., 1980.
Rosenberg et al., *J Immunol*, 185:560-8, 2010.
Schenkman et al., *Ann Rev Microbiol*, 48:499-523, 1994.
Schijman et al., *Am J Trop Med Hyg.*, 70:210-20, 2004.
Sidney et al., *BMC Immunol*, 9:1, 2008.
Stewart & Young, In: Solid Phase Peptide Synthesis, 2d. ed., Pierce Chemical Co., 1984.
Stites, *J. Mol. Biol.*, 235(1):27-32, 1994.
Sullivan et al., *J Immunol*, 187:1358-68, 2011.
Sullivan et al., *J Immunol*, 2015.
Takada et al., *J Clin. Microbiol.*, 33(3):658-660, 1995.
Tam et al., *J. Am. Chem. Soc.*, 105:6442, 1983.
Tarleton, *J Immunol*, 144:717-24, 1990.
Viotti et al., *Ann Internal Med*, 144:724-34, 2006.
WHO. Neglected tropical diseases, hidden successes, emerging opportunities. Geneva, Switzerland: World Health Organization, 2009.
Wizel et al., *J Immunol*, 159:6120-30, 1997.
Yamamoto et al., *Jpn. J. Cancer Res.*, 79:866-873, 1988.
Yin et al., *J. Biol. Resp. Modif.*, 8:190-205, 1989.

The invention claimed is:

1. A method of inducing an immune response in a subject comprising administering to a subject one or more peptides comprising an amino acid sequence selected from the group consisting of SEQ ID NO: 1-5 and 7-30, wherein (a) at least one trans-sialidase peptide and one non-trans-sialidase peptide are administered; (b) at least one functional trans-sialidase peptide and at least one non-functional trans-sialidase peptide are administered; (c) at least one functional trans-sialidase peptide and at least one non-trans-sialidase peptide are administered; or (d) at least one non-functional trans-sialidase peptide and at least one non-trans-sialidase peptide are administered.

2. The method of claim 1, wherein said peptide or peptides is/are 9-15 residues in length.

3. The method of claim 1, wherein said peptide or peptides is/are fused to another amino acid sequence.

4. The method of claim 1, wherein at least 2, 3, 4, 5, 6, 7, 8, 9, 10, 11, 12, 13, 14, 15, 16, 17, 18, 19, 20, 21, 22, 23, 24, 25, 26, 27, 28, or 29 distinct peptides are administered to said subject.

5. The method of claim 1, further comprising inducing an immune response to a peptide comprising SEQ ID NO: 6.

6. The method of claim 1, wherein said non-trans-sialidase protein is selected from the group consisting of cruzipain precursor, surface protease GP63, histone H3, ATP synthase, citrate synthase, pitrilysin-like metalloprotease, retrotransposon host spot protein, HSP70, surafe protein ToIT, dynein light chain, *pumilio*/PUR RNA binding protein, and mucin-asociated surface protein.

7. The method of claim 1, further comprising multiple administrations.

8. The method of claim 1, wherein administration comprises injection.

9. The method of claim 1, wherein said peptide or peptides is/are administered with an adjuvant.

10. The method of claim 1, wherein the total amount of peptide administered is between 50 µg/kg and 1 mg/kg.

11. The method of claim 1, wherein said subject is a human subject.

12. The method of claim 1, wherein said subject is a non-human subject, such as a mouse.

13. The method of claim 1, further comprising measuring a $CD8^+$ T cell response in said subject following administration.

14. The method of claim 8, wherein the injection is subcutaneous, intradermal or intramuscular injection.

15. The method of claim 9, wherein adjuvant is a squalene adjuvant, a cytokine adjuvant, a lipid adjuvant or a TLR ligand.

16. The method of claim 12, wherein the non-human subject is a mouse.

* * * * *

UNITED STATES PATENT AND TRADEMARK OFFICE
CERTIFICATE OF CORRECTION

PATENT NO. : 10,821,164 B2
APPLICATION NO. : 15/738209
DATED : November 3, 2020
INVENTOR(S) : Daniel Hoft et al.

Page 1 of 1

It is certified that error appears in the above-identified patent and that said Letters Patent is hereby corrected as shown below:

In the Claims

In Claim 12, Column 38, Line 16, delete ", such as a mouse".

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*